(12) United States Patent
Gavaga

(10) Patent No.: US 10,278,799 B2
(45) Date of Patent: *May 7, 2019

(54) EMBRYO TRANSFER

(71) Applicant: Quinn A. Gavaga, Cache Creek (CA)

(72) Inventor: Quinn A. Gavaga, Cache Creek (CA)

(73) Assignee: Excipio Technologies Inc., Ashcroft (CA)

( * ) Notice: Subject to any disclaimer, the term of this patent is extended or adjusted under 35 U.S.C. 154(b) by 349 days.

This patent is subject to a terminal disclaimer.

(21) Appl. No.: 15/133,414

(22) Filed: Apr. 20, 2016

(65) Prior Publication Data

US 2016/0374786 A1    Dec. 29, 2016

Related U.S. Application Data

(63) Continuation-in-part of application No. 14/059,001, filed on Oct. 21, 2013, now Pat. No. 9,498,251, which is a continuation-in-part of application No. PCT/CA2012/050407, filed on Jun. 19, 2012.

(60) Provisional application No. 61/499,351, filed on Jun. 21, 2011.

(51) Int. Cl.
*A61B 17/435* (2006.01)
*A61D 19/04* (2006.01)

(52) U.S. Cl.
CPC ............ *A61D 19/04* (2013.01); *A61B 17/435* (2013.01)

(58) Field of Classification Search
CPC .............................. A61B 17/435; A61D 19/04
See application file for complete search history.

(56) References Cited

U.S. PATENT DOCUMENTS 4,632,110 A * 12/1986 Sanagi ................... A61B 10/02
                                                               606/207
9,498,251 B2 * 11/2016 Gavaga ................ A61B 17/435

* cited by examiner

*Primary Examiner* — Christine H Matthews
(74) *Attorney, Agent, or Firm* — Adrian D. Battison; Ade & Company Inc.; Ryan W. Dupuis

(57) ABSTRACT

An embryo from a female animal is transferred to another animal by determining presence of an embryo in the uterus of a donor animal by ultra-sonic imaging and inserting an endoscope vaginally into the uterus to a location adjacent the embryo. A tool of the endoscope projects to a position to extract the embryo washed into a container of the tool which is then closed by moving a closure part to enclose the embryo and extracting the endoscope to remove the embryo for transfer to a recipient animal. The fluid into the container can be controlled in pressure to maintain a required pressure generally matching that inside the uterus.

22 Claims, 13 Drawing Sheets

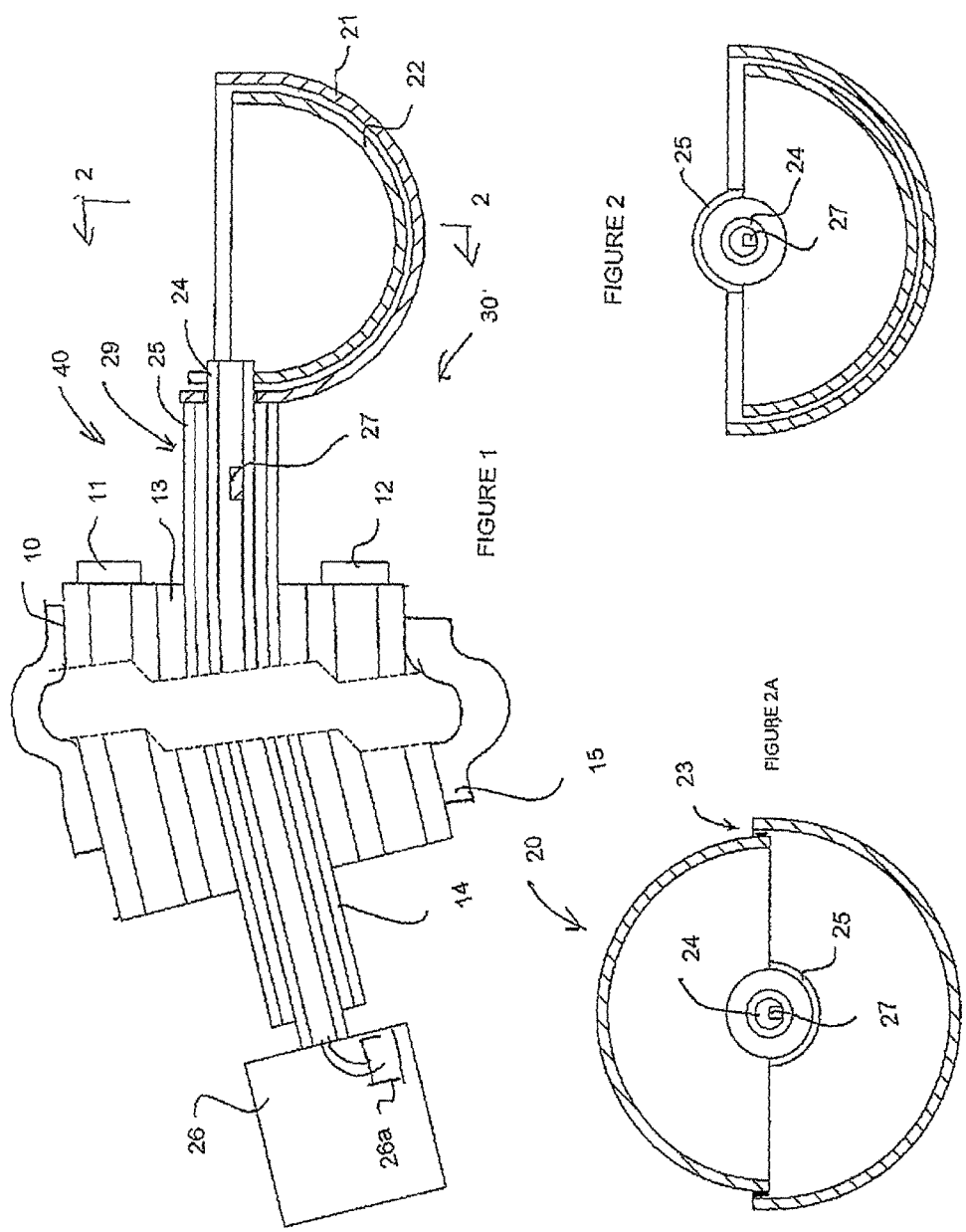

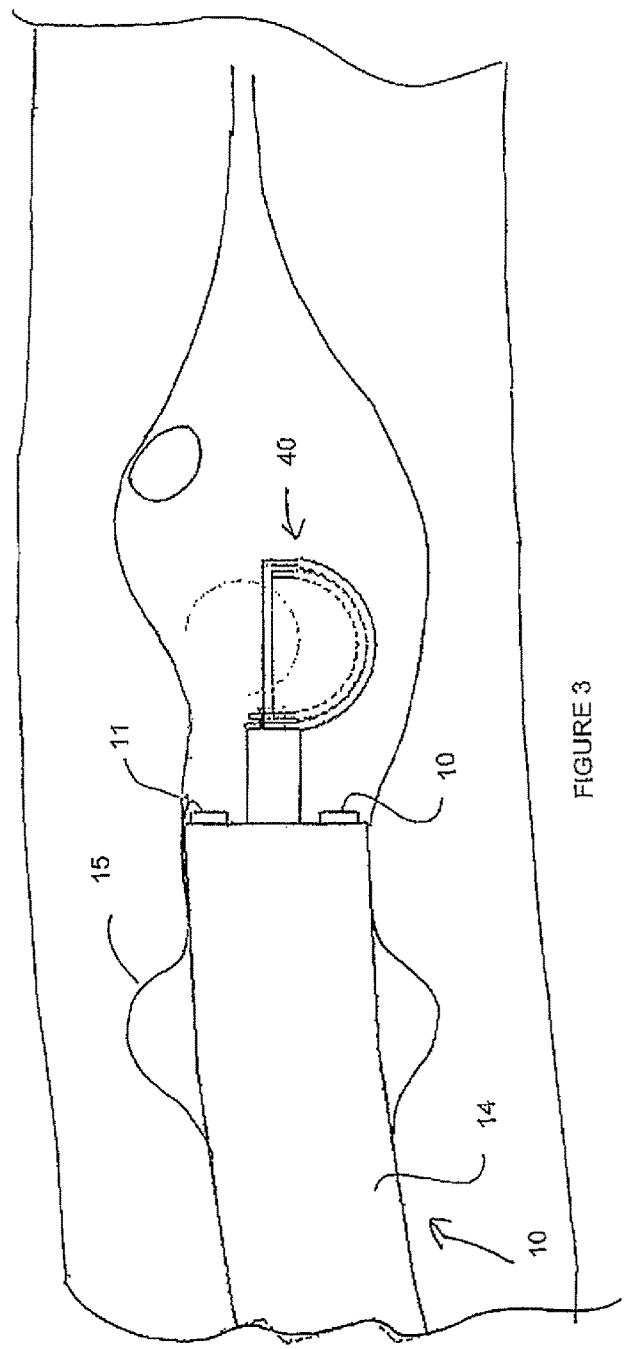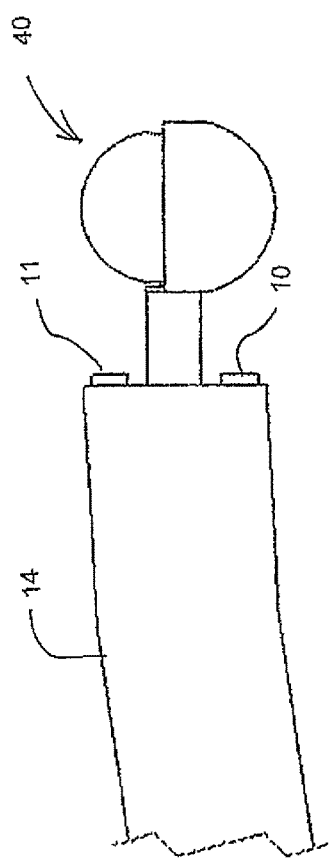

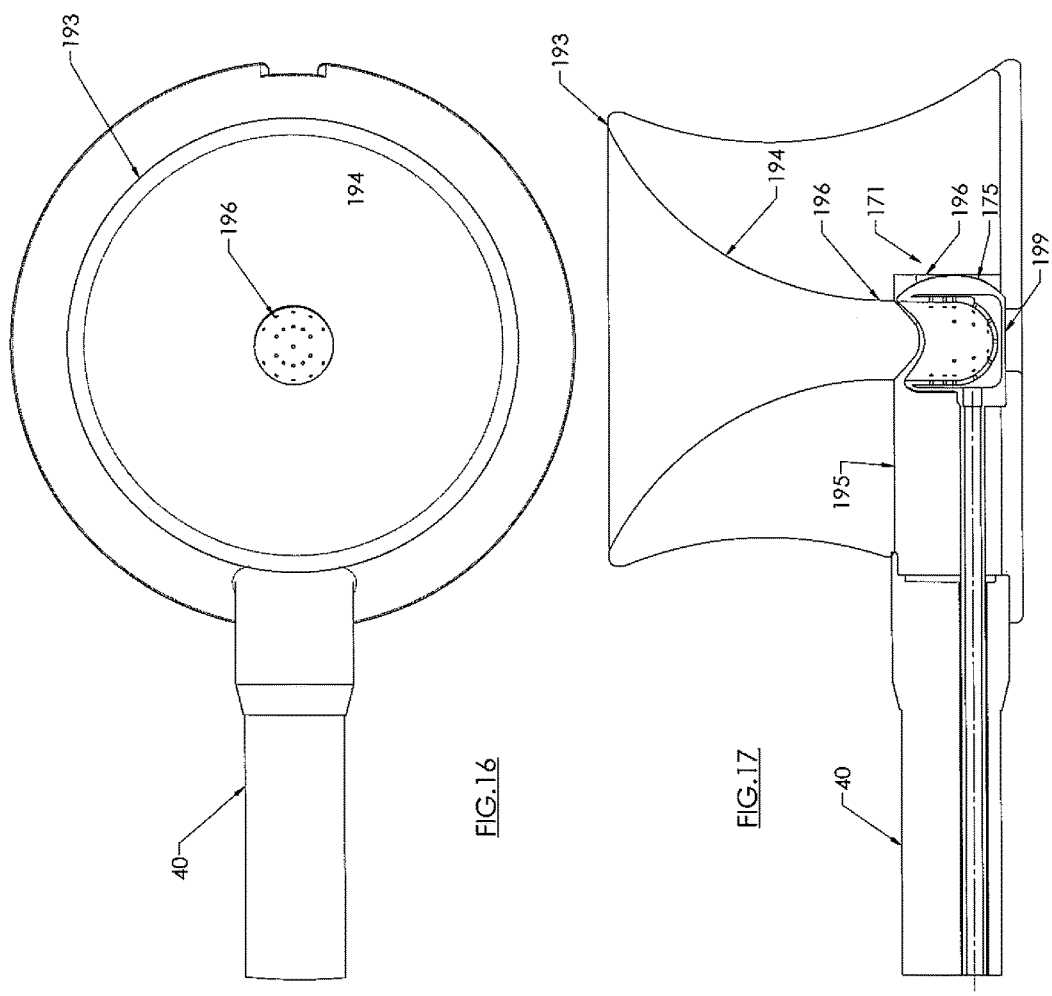

EMBRYO TRANSFER

This application is a continuation in part of application Ser. No. 14/059,001 filed Oct. 21 2013 which is a continuation in part of Application PCT/CA2012/050407 filed Jun. 19, 2012 and claims the benefit under 35 USC 119 (e) of Provisional Application 61/499,351 filed Jun. 21, 2011.

This invention relates to an apparatus and method for embryo transfer from one female mammal to another. The description hereinafter primarily relates to mares where the commercial operation of transfer methods is desirable, but ineffective; but can relate to any female mammal.

BACKGROUND OF THE INVENTION

Embryo transfer (ET) is the process of harvesting an embryo or embryos from a donor and transferring it to a recipient. The process can be done surgically or non-surgically with the latter being the preferred method in bovine and equine species and the former being the preferred technique in smaller species such as porcine, ovine, caprine and canine.

Application for ET in the mare is commercially done for three main reasons; a donor mare in competition can produce and transfer an embryo and still compete while a recipient mare carries her genetics to a term pregnancy, to produce multiple pregnancies in one year, to transfer to a recipient mare when the donor mare is considered a high risk for pregnancy complications.

In cattle superovulation is a successful procedure where with hormone therapy multiple (average 6 but numbers as high as 40 reported) embryos can be harvested (flushed) in any one procedure. Unfortunately mares do not respond successfully to superovulation so a single procedure yields at best only one embryo. The exception is when a mare naturally double ovulates and thus two potential embryos might be retrieved. The average success of achieving a pregnancy through embryo transfer in the mare is 25%. The average cost per attempt is from $7000 to $12000 and the industry reports embryo transfer in mares to be approximately $250 000 000 annually worldwide. This means that $187 500 000 is spent with no results. This poor success has hindered the process of embryo transfer in mares from becoming a more main stream procedure.

The traditional method for transferring an embryo in mares is to aseptically pass a catheter through the vulva, vagina and cervix and into the uterine body. A cuff is inflated to seal the cervical uterine junction. The uterus is flushed with approximately 4 liters of specialized solution. The solution is filtered through a 20 micron filter. The filter is emptied into petri dishes and then the dishes are searched with microscopy to find an embryo. If found the embryo is isolated and washed in another specialized solution and then loaded into a transfer pipette. The recipient mare is aseptically prepared for transfer and the transfer pipette is passed through the vulva, vagina and cervix and into the uterine body where the embryo is deposited.

Special concern for timing is required for a successful pregnancy from an ET procedure. The procedure is considered to start at day 0 which is when the mare is observed to have ovulated. The sperm must be present in the fallopian tubes prior to ovulation. Fertilization takes place in the fallopian tubes shortly after ovulation and the embryo remains there for 5 days after which time it moves into the uterus. Flushing or retrieving the embryo is normally done at day 7 which allows for adequate time for the embryo to reach the uterus for it cannot be retrieved from the fallopian tube. After day 8 the embryo hatches from its protective shell called the zona pellucita which then makes the embryo more fragile to handle. So 7 days post ovulation achieves the highest success rates thus far. A uterus is dynamic and changes through the female cycle. For this reason a recipient mare must be synchronized with the donor mare and her uterus must be close to 7 days post ovulation which adds another level of difficulty to the procedure. At the time a flush is performed it is unknown whether there is a viable embryo present or not.

Attempts have been made to transfer embryos at later stages of development such as 11 to 14 days post ovulation. At 11 days post ovulation the embryo is visible to a highly trained practitioner using ultra-sonography. This would seem to be ideal as retrieval would only be attempted if there was a pregnancy visualized. Unfortunately no success has been achieved at this stage. It is hypothesised that the embryos were too fragile and didn't survive the procedure.

SUMMARY OF THE INVENTION

It is one object of the invention to provide an improved method and/or apparatus for use in embryo transfer from a donor female to a recipient female for raising animals.

According to one aspect of the invention there is provided an apparatus for transferring an embryo from a uterus of a female donor mammalian animal in pregnancy to a uterus of a female recipient mammalian animal and raising the embryo to full term in the recipient animal, the apparatus comprising:

an endoscope having a camera;

the endoscope having a remote end of the endoscope arranged to be inserted vaginally into the uterus of the donor animal to a location adjacent the embryo on the wall of the uterus of the donor animal;

the remote end of the endoscope being operable to move the remote end to different positions within the uterus;

an elongate carrying member extending outwardly from the remote end of the endoscope;

a scoop member carried on the elongate carrying member to scoop up the embryo from the wall of the uterus;

the elongate carrying member being operable for movement in rotation about a longitudinal axis of the elongate carrying member;

the elongate carrying member being operable for movement longitudinally relative to longitudinal axis of the elongate carrying member;

and an enclosing member operable to enclose the embryo after the embryo is scooped up.

According to a second aspect of the present invention there is provided on apparatus for transferring an embryo from a uterus of a female donor mammalian animal in pregnancy to a uterus of a female recipient mammalian animal and raising the embryo to full term in the recipient animal, the apparatus comprising:

an endoscope having a camera;

the endoscope having a remote end of the endoscope arranged to be inserted vaginally into the uterus of the donor animal to a location adjacent the embryo on the wall of the uterus of the donor animal;

the remote end of the endoscope being operable to move the remote end to different positions within the uterus;

an elongate carrying member extending outwardly from the remote end of the endoscope;

a scoop member carried on the elongate carrying member to scoop up the embryo from the wall of the uterus;

and an enclosing member operable by relative movement of the enclosing member and the scoop member in a direction longitudinally of the elongate carrying member to enclose the scoop member after the embryo is scooped up.

Preferably the apparatus includes a manually operable member for actuating said movement in rotational movement and said longitudinal movement to move to the wall to scoop up the embryo.

Preferably the manually operable member comprises a handle connected to said elongate carrying member for applying longitudinal movement to the elongate carrying member and a rotatable portion of the handle for rotating the elongate carrying member. This handle can be used alongside the conventional control system for the endoscope which controls the end position of the remote end of the endoscope so that the operator can manipulate the endoscope with one hand while the handle for the movement of the scoop member is operated by the other hand to push and pull and also rotate the scoop member.

Preferably the rotatable portion forms an end portion of a cylindrical handle opposite to the elongate carrying member. This presents the rotatable and the portion the facing upwardly toward the user with the end portion being operable by the thumb of the user while the other thumb operates the controls of the endoscope.

Preferably the elongate carrying member comprises a wire. However other materials can be used or which provide sufficient stiffness and resistance to twisting to allow movement of the scoop member to the required location.

In one embodiment the enclosing member comprises a cover portion carried on the remote end of the endoscope where the scoop member is pulled into cooperation with the cover portion by retraction movement of the elongate carrying member. Thus the proportion remains fixed at the end of the endoscope rather than moving with the scoop member.

In one particular arrangement the scoop member comprises a bowl with a generally semi-spherical bottom portion forming a top edge which extends from a lower portion of the bowl at the end of the bowl adjacent the remote end of the elongate carrying member to a raised end wall portion of the bowl at the end of the bowl remote from the elongate carrying member and wherein the cover portion comprises a generally arched wall with side edges which cover the top edge of the bowl and an end edge which butts up to the raised end wall portion. This shape of the cooperation between the bowl into which the embryo is collected on the cover portion avoids or reduces the possibility for pinching of the embryo as the enclosing action takes place.

Preferably the scoop member and the remote end of the endoscope include cooperating locating members to allow engagement of the scoop member with the remote end only in a predetermined angular position of the scoop member around the axis of the elongate carrying member at which the enclosing member cooperates with the scoop member to enclose the scoop member. In this way as the scoop member is retracted, its angular position is determined by the locating members so that it only moves into engagement with the cover portion when in the orientation for proper engagement with the cover portion.

According to a third aspect of the invention there is provided an apparatus for transferring an embryo from a uterus of a female donor mammalian animal in pregnancy to a uterus of a female recipient mammalian animal and raising the embryo to full term in the recipient animal, the apparatus comprising:

at least one endoscope having a camera;

said at least one endoscope having a remote end of the endoscope arranged to be inserted vaginally into the uterus of the donor animal to a location adjacent the embryo on the wall of the uterus of the donor animal;

the remote end of said at least one endoscope being operable to move the remote end to different positions within the uterus;

a first tool carried on said at least one endoscope to pick up the embryo from the wall of the uterus of the donor animal;

a second tool carried on said at least one endoscope to deposit the embryo onto the wall of the uterus of the recipient animal;

and a transfer device to transfer the embryo from the first tool to the second tool.

Preferably the same endoscope is used for both operations so that each of the first and second tools has a coupling for releasable and replaceable attachment to the endoscope. However in some arrangements to separate systems may be provided for the separate operations of the extraction and insertion.

Preferably each of the first and second tools is carried on a respective first and second elongate carrying members for insertion into the endoscope. Thus for proper operation of the two separate systems, the first carrying member is a wire and second carrying member is a tube for passage of fluid. As typically no fluid is required for injection into the bowl of the scoop member or collecting member, the use of a wire provides a better control over the position of the scoop member within the uterus. It will be appreciated that accurate control of the scoop member is required so as to ensure that it operates to scoop the embryo from the wall of the uterus without damage. This control uses both the longitudinal and rotational movement of the scoop member to bring it to the required position. At the required position rotational movement of the scoop member around the axis of the wire act to lift the embryo from the wall so that it falls into the bowl for collection.

Preferably therefore the wire is mounted on a manipulation handle for rotation and longitudinal movement and simply the tube is mounted on a syringe. Thus the insertion process requires merely that the bowl forming the insertion device is moved into the required position suitably located within the uterus and is then inverted and the fluid actuated to eject the embryo from the bowl. Accurate control of the position is thus reduced in this operation.

Thus preferably the second tool comprises a bowl into which the embryo is deposited, the bowl having fluid discharge holes for injecting discharge fluid into the bowl to expel the embryo.

In order to transfer the embryo from the first tool or scoop member, there is provided a transfer device which comprises a funnel with a transverse mounting channel for the second tool. Preferably the embryo from the scoop member is decanted in to a separate fluid such as in a petri dish to ensure that the embryo is maintained in a fluid condition against any possible drying. This combined fluid is then poured into the funnel and runs into the bowl of the second tool while the bowl is contained in the channel at the bottom of the funnel to deposit the embryo with excess fluid spilling over the sides of the bowl for discharge at the bottom of the funnel.

In another embodiment the container includes two hemispherical parts which rotate, or one of which rotates relative to the other from a first open position with one cupped inside the other to a closed spherical position sealing around the edges of the two parts. Other closure systems can be used for example a sliding sleeve arrangement around an inner tube which has a hole to collect the embryo.

Optionally there is provided a fluid supply duct for supplying fluid to the tool where the fluid supply duct opens into the closed container. In this case, there can be provided a pressure sensor for controlling pressure of the fluid inside the container to match that in the uterus. Pressure control may or may not be necessary within the closed scoop.

Preferably the container has a transverse dimension of at least 1.0 cm and preferably of the order of 1.5 cm.

Preferably the presence of the embryo is detected at a time period of the order of 11 days after insemination.

Preferably the endoscope is guided to a position within the uterus by passing through a separate guide tube inserted into the uterus through the vagina.

Preferably the guide tube is held against bending during operation of the tool so as to locate an end of the guide tube at a fixed position within the uterus. That is the guide tube is either rigid so that it cannot bend at all, or is semi-rigid so that it is adjustable in shape by bending at one or more points along its length but that it maintains that shape when in use, that is as it is inserted into the uterus through the vulva, vagina and cervix and during insertion and operation of the endoscope and tool.

It will be appreciated that the guide tube is typically inserted and guided manually by the veterinarian in many cases by feeling the position of the guide tube within the vagina of the animal by a hand inserted through the rectum. That is the end of the guide tube can be carefully guided and moved to its position within the uterus by the veterinarian feeling exactly where that end is in relation to the cervix.

The shape and arrangement of the guide tube is arranged so that the guide tube is held fixed relative to the uterus during operation of the tool so as to locate an end of the guide tube at a fixed position within the uterus. This provides a fixed point or basis for the functioning of the operating components of the endoscope for moving an end of the endoscope relative to an end of the guide tube with the end of the guide tube held in fixed position relative to the uterus. In this way the skilled veterinarian can operate the conventional operating components of bend, orientation and displacement of the end of the endoscope to accurately locate the end of the endoscope at a required position relative to the wall of the uterus.

Preferably the guide tube is held fixed relative to the uterus by locating the guide tube at the cervix.

Preferably the guide tube is located at the cervix by first and second inflating balloons with one inside the uterus at the cervix and the other outside the cervix in the vagina.

In accordance with another important feature of the invention there is provided a tube which is inserted through the vagina into the uterus and acts for guiding the endoscope to a position within the uterus by holding the guide tube fixed relative to the uterus during operation of the tool so as to locate an end of the guide tube at a fixed position within the uterus.

Preferably the guide tube is held against bending during operation of the tool so as to locate an end of the guide tube at a fixed position within the uterus.

Preferably the guide tube is held fixed relative to the uterus by locating the guide tube at the cervix.

Preferably the guide tube is located at the cervix by first and second inflating balloons with one inside the uterus at the cervix and the other outside the cervix in the vagina.

Preferably the endoscope and the tool are inserted into the guide tube when the guide tube is in fixed position with the end of the guide tube within the uterus.

Based on the augmentation and refinement to the method of embryo described herein, retrieval at 9 to 13 days and more preferably 11 or 12 days can achieve success rates in excess of 80%.

In the equine uterus a cascade of events begins in which, if no embryo is present, the uterus undergoes changes and the reproductive system starts the process toward ovulation. If a viable embryo is present in the uterus it blocks the hormone and chemical pathways that initiate the cascade to ovulation thus pregnancy is maintained. At the time of transfer on day 11 or 12 the recipient's reproductive track is already undergoing changes that may make it unable to maintain a pregnancy.

In the present method, the recipient and the donor both are bred at the same time and an embryo is removed from the recipient mare and exchanged for an embryo from the donor mare. The delicate nature of the embryo is a very important consideration for success of this procedure so highly specialized equipment has been designed to overcome this.

Using this modified embryo transfer technique the procedure is cost effective and is a more attractive method of breeding in the equine industry.

BRIEF DESCRIPTION OF THE DRAWINGS

One embodiment of the invention will now be described in conjunction with the accompanying drawings in which:

FIG. 1 is a vertical cross sectional view through a tool for use in an endoscope for extraction of an embryo, showing the tool in an initial open position.

FIG. 2 is a cross-sectional view along the lines 2-2 of FIG. 1.

FIG. 2A is a cross-sectional view along the lines 2-2 of FIG. 1 showing the tool in the closed position after collection of an embryo.

FIGS. 3 and 4 show the operation of the tool in a method of extraction.

FIG. 16 is a top plan view of the transfer device of FIG. 15.

FIG. 17 is a cross-sectional view of the transfer device with the insertion tool located therein.

In the drawings like characters of reference indicate corresponding parts in the different figures.

DETAILED DESCRIPTION

Figure 5:
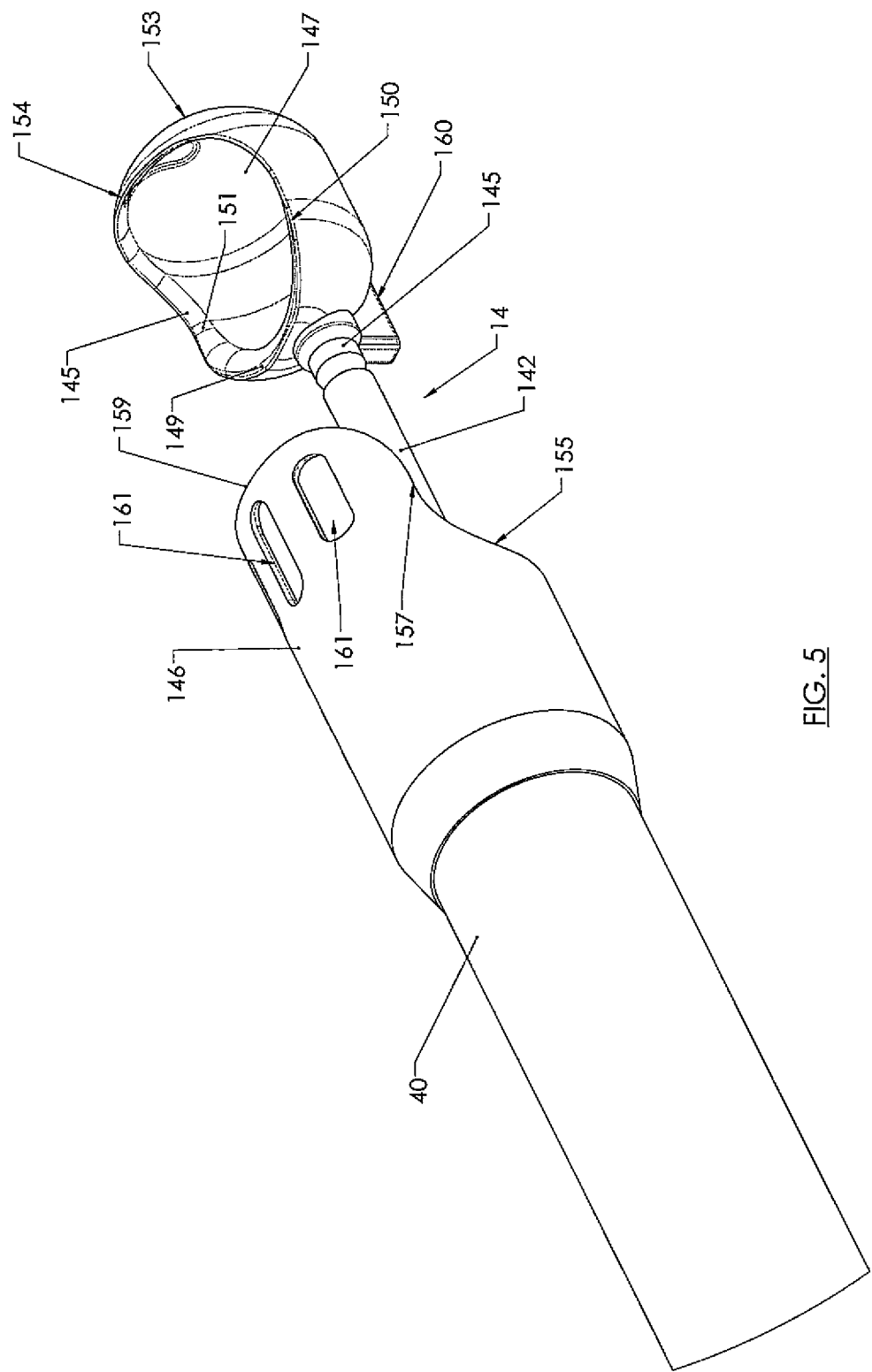
FIG. 5 is a vertical cross sectional view through a second embodiment of tool for use in an endoscope for extraction of an embryo, showing the tool in an initial open position for insertion through the tube of the endoscope.

Endoscopes are a well known device widely used in surgery and other procedures and comprise a tube with a camera and illumination which can be passed through an opening into the interior of the body and which can be manipulated to different positions. A central bore allows a tool to be passed through the tube for acting on the interior, many different tools are available. Typically a collar is provided which can be inflated to locate the tube at a required portion and to seal the opening relative to the tube. Arrangements of this type are widely used and well known to persons skilled in the art so that further details are not required.

FIG. 1 shows one embodiment of a recovery tool for use as part of a modified endoscope 40 including a tube 10 with a camera lens 11 and an illumination source 12 carried on the tube and including fiber optic communication from a distal end 10A of the tube 10 to control systems of the endoscope and the near end for operation by the user. The tube 10 is arranged so that it can be passed through an opening, in this case the vagina into the interior of the body. The tube includes components (not shown) which allow the end 10A to be manipulated to different positions. One or more central bores 13 or ports allow a tool 14 to be passed through the tube. Typically a collar 15 is provided which can be inflated to locate the tube at a required portion and to seal the opening, in this case the uterus, relative to the tube.

Through one of the working ports 13 of the endoscope is inserted a grasping tool 30. The grasping tool is small globe 20, approximately 1.5 cm in diameter. The globe has two hemispherical halves 21 and 22 one of which rotates by sliding slides inside the other. The components are made out of surgical grade stainless steel.

When closed as shown in FIG. 2 the two parts 21 and 22 form a sealed unit or globe 20 with a sealing edge 23. The inner part 22 is rotated around the axis of the sphere by an operating element 24 at the end of the tube 10 which is operated by a control at the near end of the tube from the open position where the inner part is wholly within the outer part to form a hemi-spherical scoop to a closed position in which the globe is closed and sealed. This globe also has a fluid port 25 within it so fluid can be added or withdrawn from the globe 20. The fluid supply system 26A of a control unit 26 for supply to the port 25 passes through the tube 14 and includes an inline pressure sensor 27 sensitive to the internal pressure in the line and therefore within the closed globe 20. The supply 26A of the control unit 26 can be operated so that holding fluid can be supplied or removed to adjust the internal pressure in the globe 20 to match the same pressure as that of a normal uterine environment for that stage of embryo. The pressure within the uterus can be measured in situ or can be predetermined from historical measurements.

The special tool described above can in some embodiments be used with a stock endoscope. The tool can alternatively be a permanent "biopsy tool" which is manufactured by assembly into place in an endoscope from a typical supplier, but where the tool is not be able to be removed after it is manufactured into the scope. This is due to the fact that the typical globe is too large for the portal through the tube of a typical endoscope.

The tool operates in a similar manner to an ice cream scoop. In the open position one half of the globe 20 is rotated inside the other half as shown in FIG. 2A. The neck 29 of the tool that passes through the endoscope portal 13 is formed from two flexible tubes 25 and 24 one inside the other. The outer tube 25 is fixed to the bottom half 21 of the globe and the inner tube 24 is fixed to the top half of the globe. At the operator end the user operates the device 26 by activating a turning movement to the inner tube 24 so that it rotates the top half of the globe to close it. The inner tube 24 also provides the fluid port which is optional.

When the tool is first inserted as shown in FIG. 4 in the open position and the collar 15 inflated to hold the tool in place, once the tool is passed into visual proximity of the embryo it can be used to pick up the embryo.

Endoscopes have the ability to pass fluid through the port 13 or through a separate special port (not shown) to dilate the inside of the tube 14 or open the lumen of the uterus.

Thus most endoscopes have a small port adjacent to the lens. This port typically has a very small metal deflector that directs water across the lens to clean it should it become obscured with mucus or other debris. The air required in the present method can also be passed through this port. There is a pump on the power unit that works the scope. At the operator end there is a two stage valve that is normally worked by the index finger. With light depression air is pumped through the port adjacent to the lens that is normally used for insufflation to allow for dilation which enhances passage of an endoscope. If the valve is fully depressed fluid is pumped through to clean the lens.

This fluid supply through the endoscope is used to open the uterus and to infuse a small amount of fluid into the uterus to float the embryo away from the tissue of the uterus wall so that it can be simply picked up with the scoop. Air or air and fluid may be used to insufflate the uterus to allow for better visualization and pull the majority of the endometrium away from the embryo. Fluid may then be used to completely free the embryo or the tool can be used to pick up the embryo at that point, if its positioning is good and endometrial contact is minimal.

Once the embryo is in view the cuff 15 is inflated so that if further fluid is infused the embryo will not float away. When insufflation is normally done there is constant loss of air along the outside of the scope but once the embryo is in view, the cuff 15 is inflated so constant insufflation is no longer needed and dilation of the uterus can be static.

It is necessary to control the supply and volume of fluid to prevent the embryo from floating too far away. In normal instances, because the pressure in the inflation collar 15 is kept low, the natural closure/collapse of the tissue of the uterus around the collar and the tool keeps a partial seal around the instrument and provides a slope running away from the collar 15 to prevent the embryo from falling into the area of the collar 15 where it become impossible to retrieve. The injection of fluid through the endoscope typically is required because of the fragile and movable nature of the embryo. In FIG. 4, the inflation collar 15 is close to the end of the endoscope at the location of the tool since this better locates the tube 14 and allows better control over movement of the tool. The third fluid supply tube 25 is optional but when provided acts to bathe the embryo.

When the embryo has been picked up, the tool is retracted from the donor animal and moved to the recipient. Once the embryo is placed in the recipient and the globe re-opened to release the embryo, fluid can be infused into the bottom of the globe and the embryo floated out.

The complete procedure is as follows:

1. The donor mare is synchronized in her estrous cycle with recipient mare sufficiently that they are in synchronism; or the recipient can be as much as 24 hours ahead or 72 hours but preferably not more than 48 hours behind the donor mare in her ovulation.

2. Both mares are bred on their synchronized ovulation as per normal breeding methods.

3. At earliest possible time post ovulation an embryo is searched for via ultrasonography in both the donor and recipient mares. Currently this is carried out at day 11 post ovulation when the embryo is sufficiently large to be determined by this method.

4. Once pregnancy is confirmed by the ultra-sound image in both the donor and recipient the embryo transfer and exchanged is commenced.

5. The donor and recipient mares are prepared pre-embryo recovery for a normal aseptic embryo recovery technique. Ideally the recipient mare is pregnant but that is not absolutely necessary. This transfer can still be attempted if the recipient is not pregnant but still in synchrony with the donor.

6. The procedure starts with the recipient where the recipient is sedated for ease of recovery and transfer.

7. In the recipient, a first technician operates the ultra-sound imaging system to locate and document where the embryo is residing.

8. A second technician passes the recovery scope vaginally using normal aseptic palmed delivery to the cervix and the cervix is digitally enlarged and the scope is then advanced through the cervix and the operators hand is removed. The scope is then advanced until it appears on the ultrasound adjacent to the embryo. The ultrasonographer may or may not stop at this time. One the embryo is found via ultrasound the ultrasound is removed and the perineum washed thoroughly and the scope is passed into position.

9. Once the scope is in view with the embryo, the uterine horn is insufflated by air or air and fluid supply enough to free the majority of endometrial contact with the embryo. The uterus is infused with the fluid through the supply tube 25 with a fluid, such as a commercially available embryo recovery medium, to float the embryo. The inflation cuff 15 on the end of the recovery scope is arranged to prevent washing the embryo away. The embryo is captured with the grasping tool 20 on the recovery scope. The grasping tool 20 on the working end 10A of the recovery scope 10 is now a closed and is infused with the commercially available embryo holding fluid. The recovery scope is withdrawn from the uterus. From the recipient animal, the embryo is discarded or kept for other purposes.

10. The step 9 is repeated with the donor mare.

11. The recovery scope is washed with warmed alcohol and then 1 liter of warmed saline 12. The recipient mare is sedated again if necessary and her perineum washed again.

13. The recovery scope, now containing the donor's embryo is passed using normal aseptic palmed delivery to the cervix and the cervix is digitally enlarged 14. The recovery scope is then advanced to the location from where recipients own embryo was removed. The embryo is deposited in the uterus at the bifurcation of the uterine horns. The grasping tool 20 is opened and the embryo is either dumped by turning the whole tool by the base tube 29 to invert the cup or expelled with fluid. The recovery scope is withdrawn and the procedure is complete.

The mare is checked via ultra sound immediately after the procedure for embryo placement. The mare is checked by ultrasound imaging at 6 and 24 and 48 hours post-transplant for embryo viability and procedure success.

Turning now to FIGS. 7 to 10, there is shown the tool 14 inserted through the endoscope 40 which is guided to a position within the uterus 62 by a guide tube 50 inserted into the uterus 62 through the vulva 60, the vagina 61 and the cervix 63.

The guide tube is rigid during insertion and during operation of the endoscope 40 and tool 14 so as to locate an end 51 of the guide tube 50 at a fixed position within the uterus 62. Guiding to the required position is controlled by the veterinarian by holding the proximal end 52 and by feeling the location of the distal end 51 relative to the cervix through the bowel wall.

After insertion, the guide tube 50 is held fixed relative to the uterus during operation of the tool so as to locate an end of the guide tube at a fixed position within the uterus by locating the guide tube at the cervix. The guide tube is located at the cervix by first and second inflating balloons 53, 54 on an exterior surface of the tube 50 with one 54 inside the uterus at the cervix and the other 53 outside the cervix in the vagina. Thus the cervix is located between the two balloons to prevent longitudinal movement of the tube when the balloons are inflated. Also the cervix is relatively stiff and positioned at a fixed location relative to the interior wall of the uterus so that the tube is held at a fixed location to allow the veterinarian to operate the endoscope to locate its end at a required position adjacent the wall of the uterus.

The endoscope 40 includes operating components for moving an end of the endoscope relative to an end of the guide tube with the end of the guide tube held in fixed position relative to the uterus.

The balloons 53, 54 are defined on an outside of the body of the tube 50 by a layer of a resilient material 55 covering the body of the tube 50 which is cast in place or applied to define a passage 56 from the end 52 to the first of the balloons which then communicates with a passage 56A to the end balloon. The balloons are formed by thinner annular sections of the covering 55 so that the annular sections inflate preferentially relative to the remainder of the covering to form annular balloons surrounding the tube body and extending over a limited extent longitudinally of the tube. The spacing between the balloons is designed to match approximately the thickness of the cervix to hold the cervix between them. In this way the balloons are inflated by an inflation pump 57 when the veterinarian has determined that the tube is at the required location to hold the tube at fixed position longitudinally and radially.

The balloons can be inflated independently by separate passages if required which can be used to locate the tube more effectively by locating it from one side of the cervix before the second balloon is inflated.

The endoscope is then inserted into the guide tube when the guide tube is in fixed position with the end of the guide tube within the uterus.

The endoscope 40 includes a conventional control system 45 operable by the veterinarian including operating components of the endoscope. These include a fluid supply 41A for supply of a fluid to the end of the endoscope at a nozzle 41; a gas supply 42A for supply of a gas to the end of the endoscope at a nozzle 42; a camera control 11 A for operating the camera 11 and a light control 10A for operating the illumination 10. The endoscope also includes a manually operable control 43A for operating bending elements (not shown) for bending the end of the endoscope to sides of an axis of the tube 50. Typically this is effected by a wire pulling system which pulls on the end differentially to effect bending to one side. In addition the control system can be manually moved longitudinally as indicated at 47A to push the end in and out of the tube 50 longitudinally as indicated at 47. Also the control system can be manually rotated angularly around the axis of the tube 50 as indicated at 48A to rotate the end as indicated at 48. These controls thus allow movement of the end of the endoscope to required positions within the uterus relative to the fixed or stable end of the guide tube which is held in fixed position relative to the uterus. The tool 14 can be inserted after the required adjustment movement or can be in place while that movement is being effected.

Figure 10:
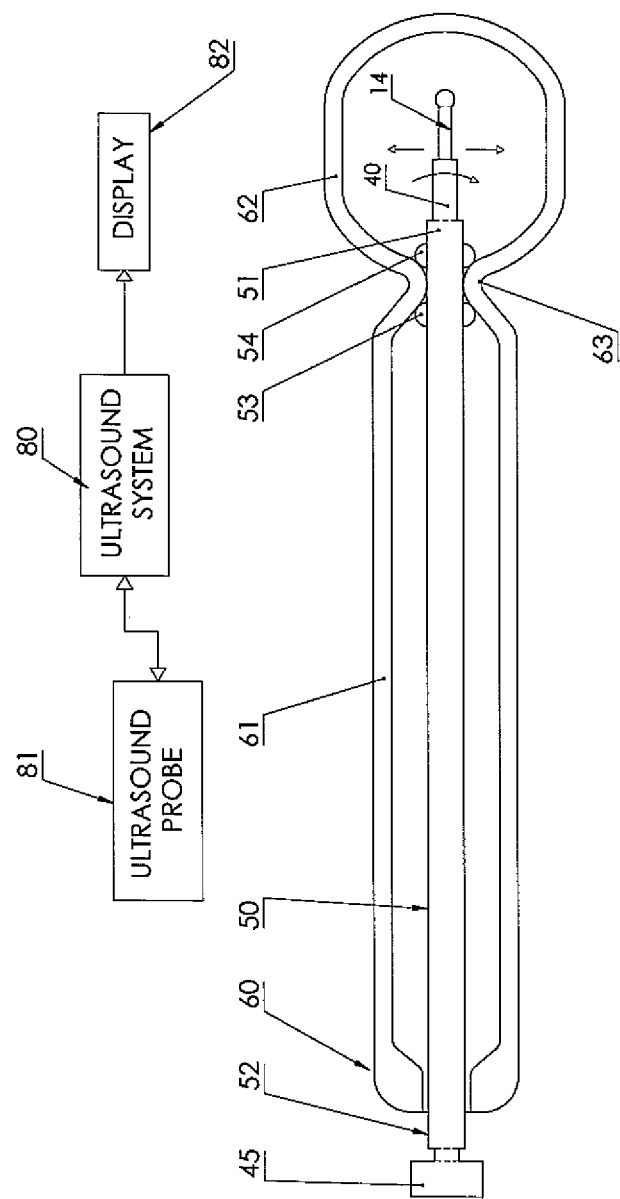
FIG. 10 is a vertical cross sectional view on a reduced scale the tube of FIG. 1 together with the endoscope and the tool of FIG. 1 showing the components in position inserted through the vulva, vagina and cervix of the animal into the uterus.

The ultrasound system for guiding the extraction of the embryo by the veterinarian is schematically illustrated in FIG. 10 at 80 and includes a probe 81 and a display 82. This enables the veterinarian to view the position of the embryo and to use the tool to extract the embryo as previously described.

Figure 6:
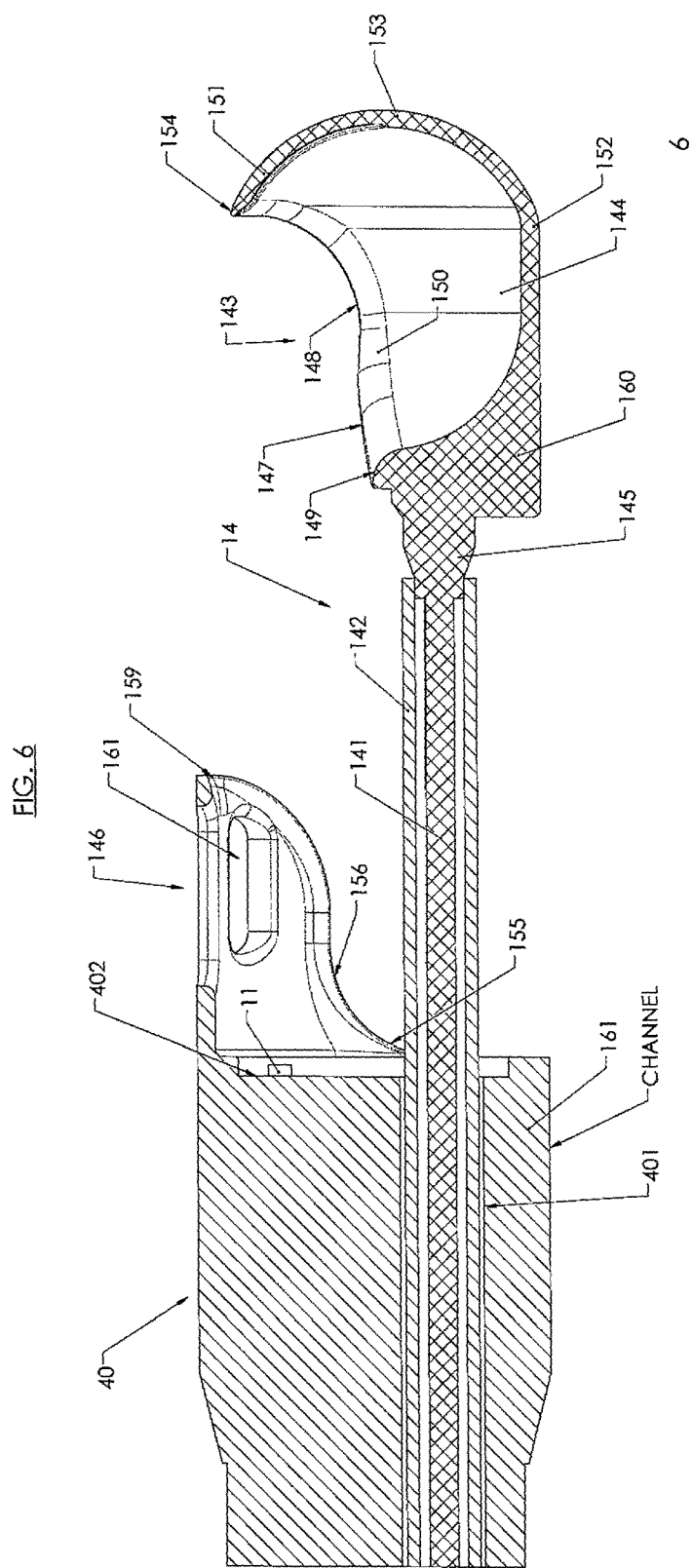
FIG. 6 is a cross-sectional view through of the tool of FIG. 5 in the open position.
Figure 7:
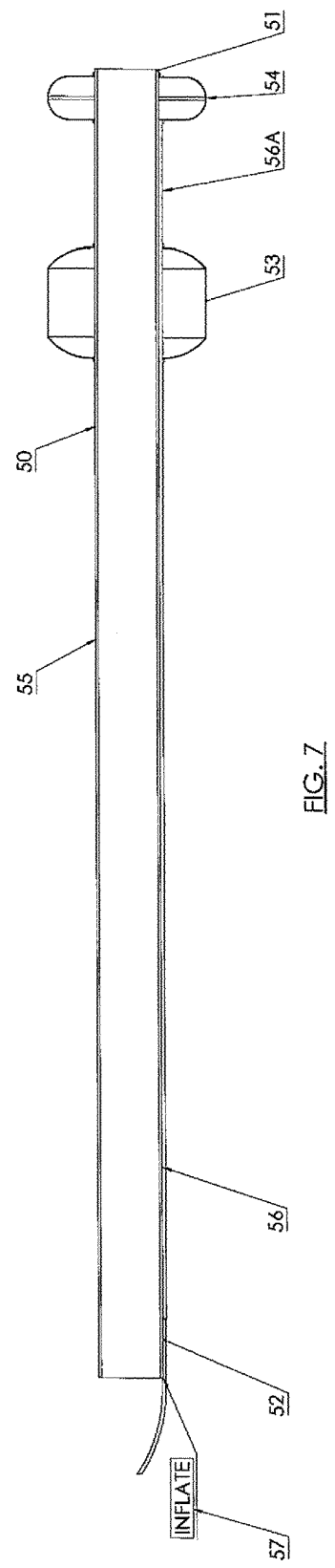
FIG. 7 is a vertical cross sectional view through a tube for locating within the uterus of the animal the endoscope and tool of FIG. 1 for extraction of an embryo.
Figure 8:
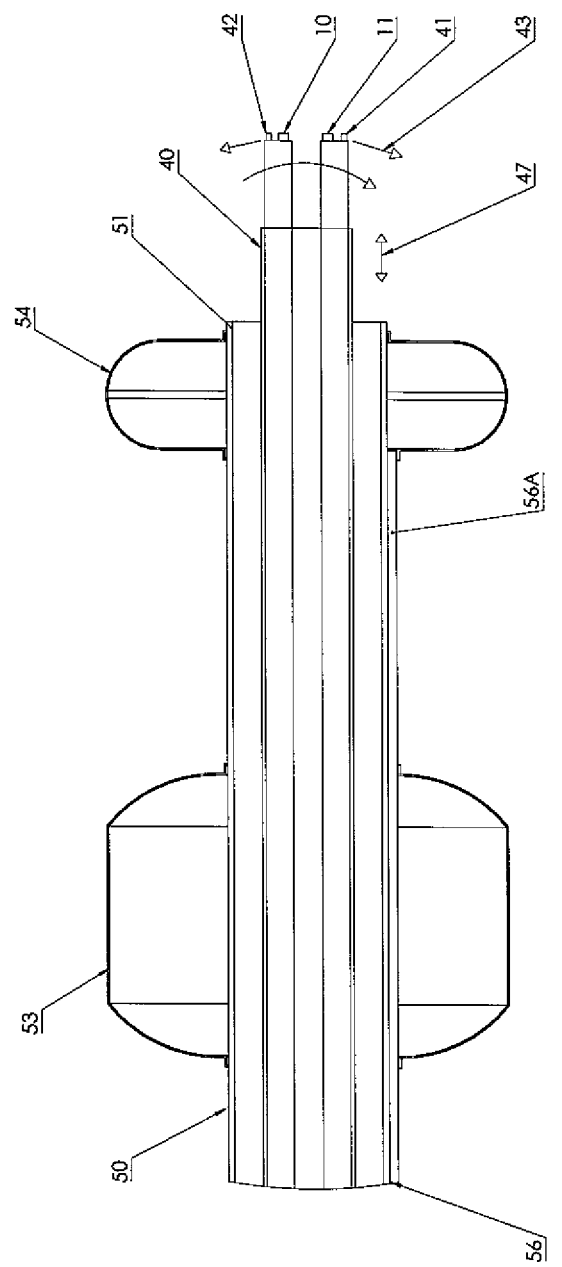
FIG. 8 is a vertical cross sectional view on an enlarged scale through the remote end of the tube of FIG. 1 showing the insertion and operation of the endoscope.
Figure 9:
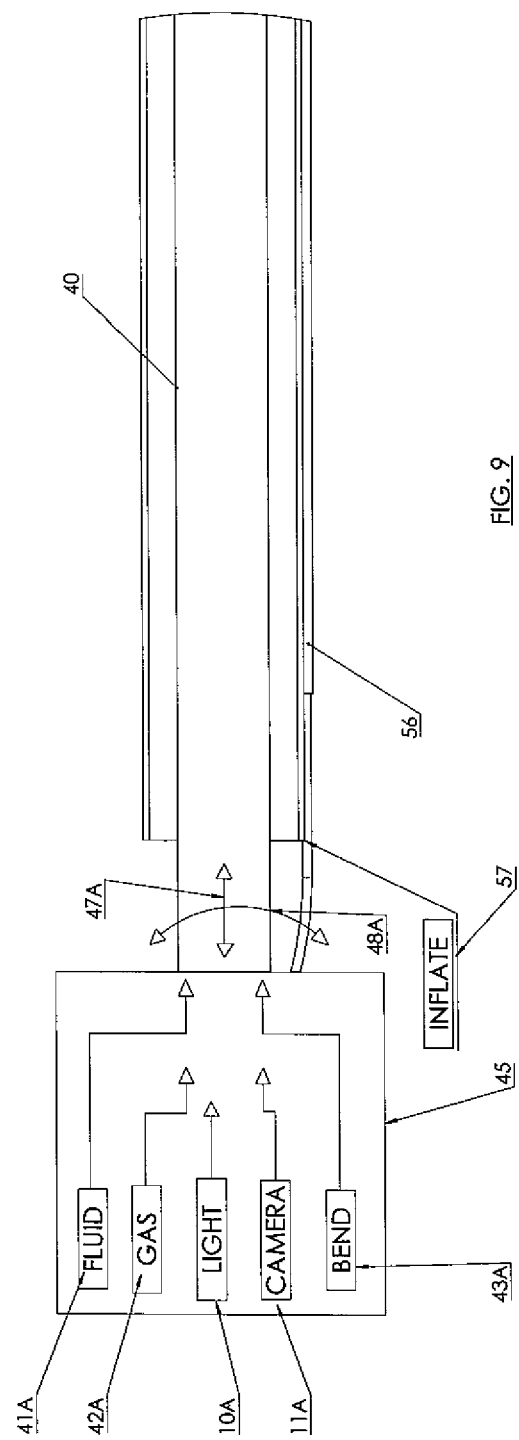
FIG. 9 is a vertical cross sectional view on an enlarged scale through the proximal end of the tube of FIG. 1 showing the control system of the endoscope.

Turning now to FIGS. 5 and 6, one embodiment of a tool 14 for extracting the embryo is shown which is inserted through the bore 401 of the endoscope 40. The tool 14 comprises a wire 141 inserted within a plastics tube 142 so that the wire and tube can slide readily through the bore 401 of the endoscope.

The tool 14 further includes a scoop member 143 in the form of a bowl 144 with a mounting end 145 of the bowl attached to the wire 141 and to the tube 142. The mounting at the head 145 can be a permanent coupling ensuring fixed connection of the scoop member to the wire or it can be a removable coupling such as a threaded connection which allows the scoop member to be removed from the wire and replaced. This removal can allow the wire and tube to be pulled out through the endoscope from the operating end so as to avoid removing the handle. However in an arrangement where the scoop member is permanently attached to the wire, this connection at the handle end allows the wire to be pulled through the endoscope in the forward direction.

The scoop member 143 cooperates with a cover portion 146 attached to the end 402 of the endoscope. The cover portion 146 is fixed to the endoscope so it remained in position as the scoop member is moved forwardly and rearwardly on the wire. In the open position shown in FIGS. 5 and 6, the scoop member is moved away from the cover portion so that it has an open mouth 147 defined by a top edge 148.

The top edge 148 has a rear end 149 adjacent the head 145 and two side edges 150 and 151. The rear end 149 on the side edges form a substantial the edge of a hemispherical bowl except that the side edges 150 and 151 incline upwardly on forwardly toward the forward end of the bowl. At the forward end is formed an end wall 151 which curves upwardly and forwardly from a base 152 to a front wall is 153 and upwardly there from to a top edge 154. Thus the front edge of the bowl is the smoothly curved and defines a part spherical shape to the front wall 153. Thus the top edge 154 defines a raised edge above the side edges 150 and 151. The structure thus forms a scoop which can operate in effect in the form of an ice cream scoop so that rotational movement of the scoop member about the axis of the wire will act to lift the embryo from the wall by gentle engagement with one of the side edges 150 or 151. In the alternative the edge 154 can be used by a skilled operator using the wire to pull the scoop member rearwardly as the edge 154 moves over the wall of the uterus.

The cover portion 146 is generally arch shaped with a bottom edge portion 155 and two side edges 156 and 157 which extend upwardly on forwardly to a front edge 159. To be noted therefore that the shape of the edges of the cover portion generally match the edges of the scoop member so that when the scoop member is drawn into a position underneath the cover portion, the cover portion acts to close against the edges of the scoop member. Thus particularly the side edges of the cover portion overlie the side edges of the scoop member and the front edge 159 closes against the upper edge 154 of the scoop member. This closing action however avoids pinch points which could damage the fragile embryo. The sliding of the cover portion over the scoop member tends to push the embryo into the scoop member in the event that it is not properly contained.

In order to ensure that the scoop member and cover portion are properly aligned before they are moved together, there is provided a rib 160 underneath the scoop member must enter a channel 161 in the front of the endoscope to confirm the alignment before the components can be brought together by retraction of the wire.

The wire thus allows both rotational and longitudinal movement of the scoop member under the control of the user by the handle described hereinafter for accurate positioning of the scoop member to lift the embryo from the wall.

The cover portion 146 includes a plurality of a cutout windows or openings 161 in the arched surface which allow vision by the user from the camera lens 11 through the windows to a position above the cover portion. In this way the view by the user of the wall of the uterus is not obscured either to the sides and bottom and the reduction in vision at the top caused by the cover member is reduced.

While the location of the embryo has previously been determined approximately by the ultrasound system as previously described, it must be located visually by the camera lens 11 on the viewing system of the user to enable the user to accurately and effectively manipulate the scoop member to the required position.

Figure 11:
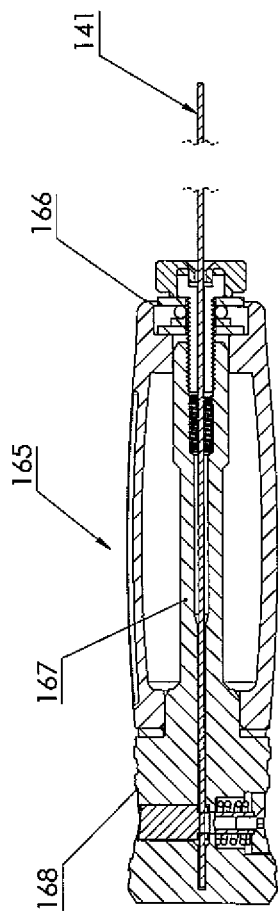
FIG. 11 is a cross-sectional view of a handle for mounting on the outer end of the wire of the scoop member of FIG. 5 for the user to operate rotational and longitudinal movement of the wire to locate the scoop member.
Figure 12:
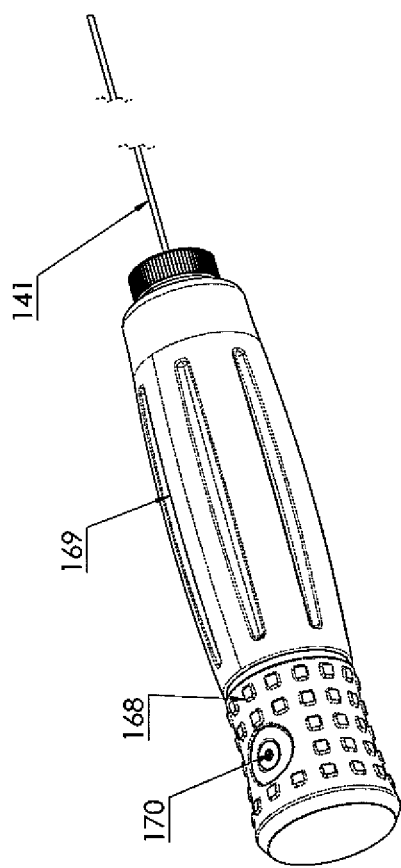
FIG. 12 is an isometric view of the handle of FIG. 11.

Turning now to FIGS. 11 and 12, a handle 165 is provided which is attached to the opposite end of the wire and tube 141. The handle includes a guide system 166 which allows the wire 141 to pass through an end face of the handle into the interior of the handle where it passes along a central bore of the handle as indicated at 167. An end piece 168 of the handle can be manually operated by the user to rotate the wire 141 around its axis within the generally cylindrical out of body 169 of the handle. A button 170 is operable by the user to lock the wire against rotation solemnity longitudinal movement as possible.

Figure 13:
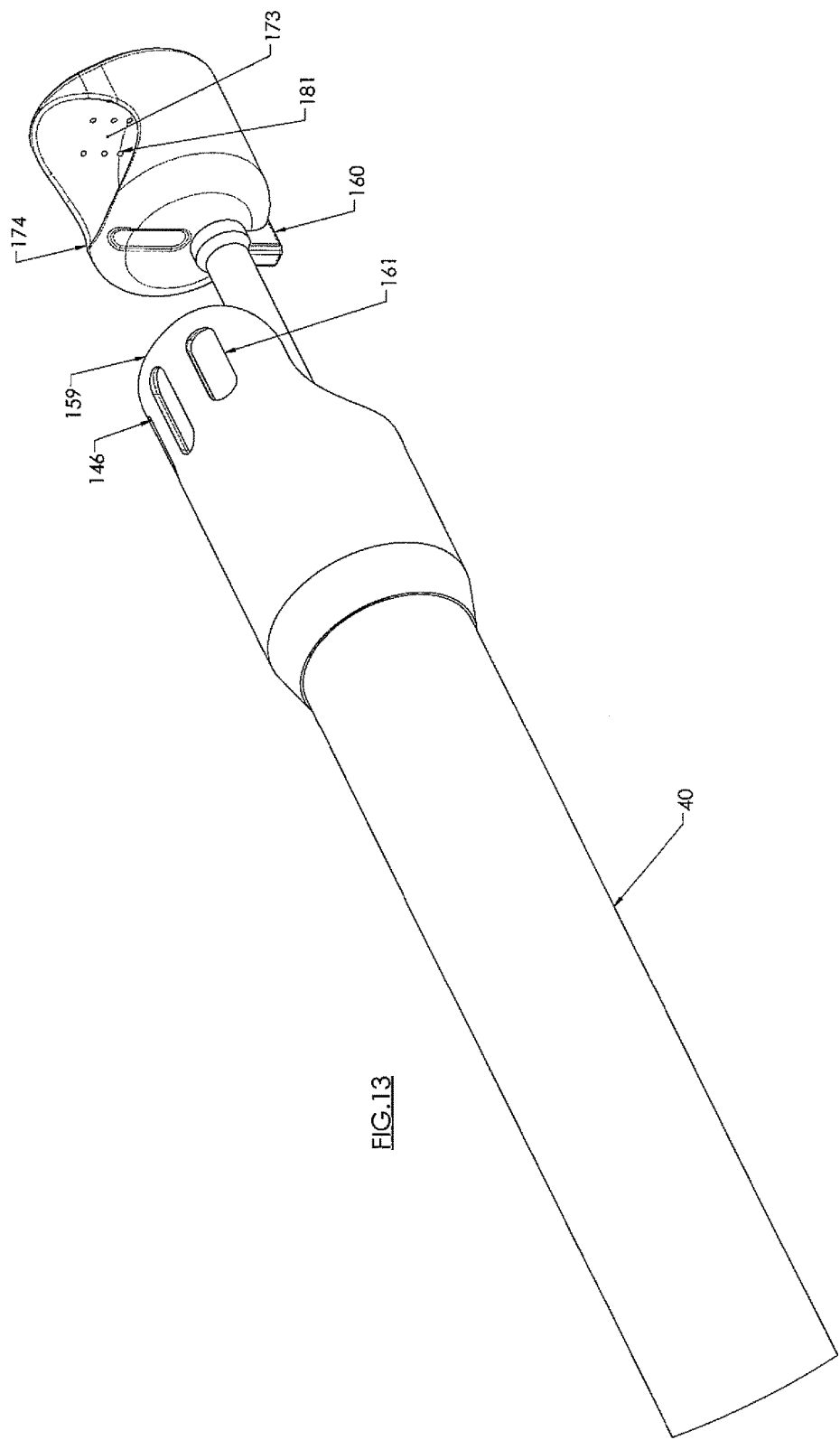
FIG. 13 is an isometric view of the second tool for deposit of the embryo into the uterus of the recipient animal.
Figure 14:
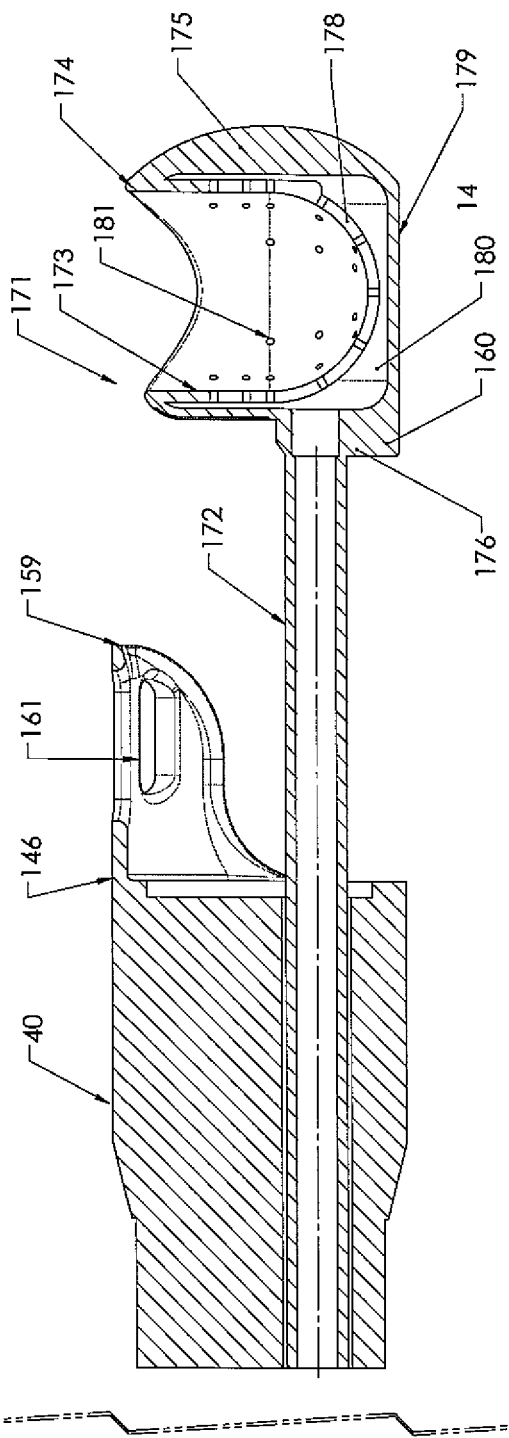
FIG. 14 is a cross-sectional view through the second tool of FIG. 13.

Turning now to FIGS. 13 and 14, there is shown the construction of the insertion device 171. The insertion device is carried on a tube 172 through which fluid from a syringe can be inserted when required. As the angular and longitudinal position of the insertion device 171 requires less accuracy, a hollow tube 172 can be used as the control device for this tool on the syringe can be used as the handle which controls its location. However the syringe can be both rotated and moved longitudinally to move the insertion device to a required position within the uterus and to invert the insertion device so that its mouth is facing downwardly by rotation around the axis of the tube. The insertion device is of similar construction to that of the scoop member in that it comprises a bowl 173 with a top opening 174. A domed end face 175 is located at the end of facing away from the tube 172. A fastening mechanism 176 is provided coupling the insertion member to the tube 172 either permanently or separably depending upon which direction the tube is removed from the endoscope 40. Typically as the syringe can be removed readily, a permanent connection at the coupling 176 can be used since the tool can be removed from the endoscope in the direction away from the syringe.

Typically the insertion tool is used with the same endoscope 40 and the same cover member 146 as the scoop member when the scoop member has been removed as previously described. However of course to separate dedicated endoscope can be provided for these two separate tools if the added expense is justified.

The top edge 174 of the bowl is arranged so that it slides readily underneath the cover member 146 up to a position where the top edge of the domed end face 175 engages the end 159 of the cover portion.

In the first position of operation of the insertion tool, therefore, the embryo is contained within the bowl 173 and is covered by the cover member 146. After the endoscope is moved into place through the tube 50 and the position of the end of the endoscope determined to be located within the uterus, typically by manual manipulation, the tube 172 is pushed outwardly to extend the insertion tool beyond the end of the endoscope thus opening the mouth of the bowl.

In this position, the bowl can be inverted so that the open mouth faces downwardly. It was noted that the bowl is formed with an inner wall 178 and an outer wall 179 forming a chamber 180 therebetween which is connected to the interior of the tube 172. Pressure of fluid from the syringe therefore enters the chamber 180 and escapes through holes 181 in the inner wall 178 thus tending to eject the embryo from the bowl to discard it gently downwardly into the uterus.

It will be appreciated that the orientation of both the insertion device and the scoop member is difficult to determine from a visual image obtained by the camera lens 11. Thus the user typically cannot see from the viewing screen the orientation of the mouth of the bowl relative to gravity. A sensor may be provided which outputs an indication of the direction of gravity so that the user can maintain the bowls with the mouth up when intending to keep the embryo within the bowl and can invert the bowl when it is required to discard the embryo. As an alternative, a release of some fluid from the endoscope fluid system will show to the user which direction the fluid falls providing a guide us to the direction of gravity.

Figure 15:
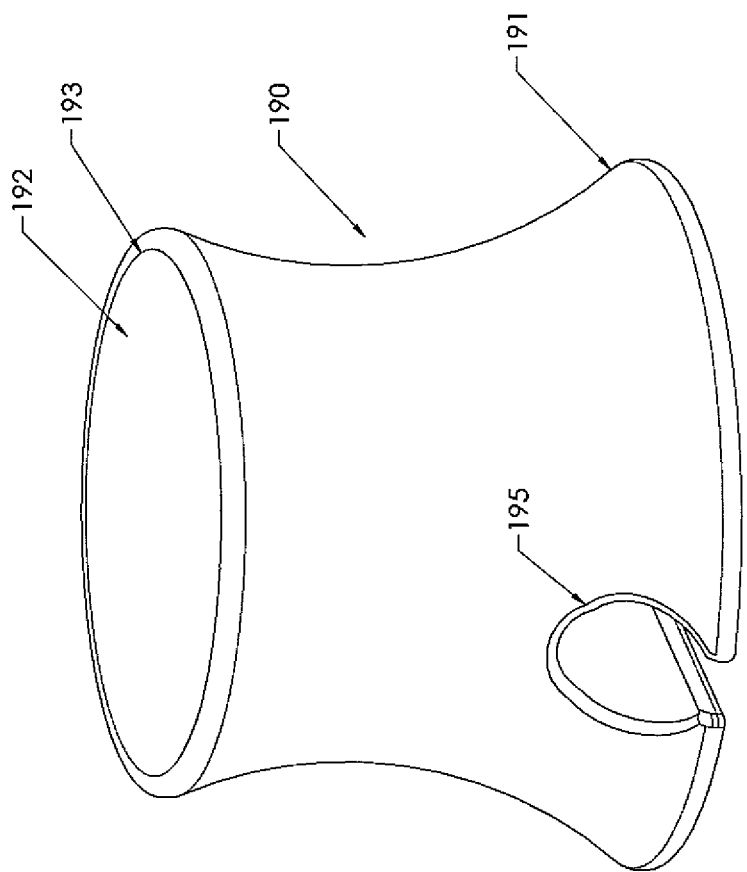
FIG. 15 is an isometric view of a transfer device or funnel for transferring the fluid and embryo from the first tool into the second insertion tool.

Now to FIGS. 15, 16 and 17, there is shown a transfer device 190 which allows the transfer of the embryo into the insertion tool 171. The transfer device 190 has a flat base section 191 which is both of the wide and heavy to maintain a stable base. At the top there is provided opening 192 with a peripheral wall 193 defining a formal 194 into which fluid can be poured. A channel 195 is provided shaped to receive the bowl of the insertion device 171 and the end of the endoscope 40. The channel terminates in the end wall 196 which abuts against the domed surface 175 of the insertion tool 171 which locates the open mouth of the bowl at the bottom mouth 196 of the funnel 194.

Typically the scoop member when retracted from of the animal is a emptied in to a suitable container of fluid to maintain the embryo in a suitable condition for insertion. About fluid containing the embryo is then poured into the open mouth 192 so the fluid runs down the funnel into the mouth of the tool 171 to ensure that the embryo enters the mouth. Excess fluid escapes along the channel 195 and through an opening 199 and the base with the fluid passing around the bowl of the insertion tool 171 for discharge.

The invention claimed is:

1. An apparatus for transferring an embryo from a uterus of a female donor mammalian animal in pregnancy to a uterus of a female recipient mammalian animal and raising the embryo to full term in the recipient animal, the apparatus comprising:
    an endoscope having a camera;
    the endoscope having a remote end of the endoscope arranged to be inserted vaginally into the uterus of the donor animal to a location adjacent the embryo on a wall portion of the uterus of the donor animal;
    the remote end of the endoscope being operable to move the remote end to different positions within the uterus;
    an elongate carrying member extending outwardly from the remote end of the endoscope;
    a scoop member carried on the elongate carrying member to scoop up the embryo from the wall portion of the uterus;
    the elongate carrying member being operable for rotational movement about a longitudinal axis of the elongate carrying member;
    the elongate carrying member being operable for longitudinal movement relative to the longitudinal axis of the elongate carrying member;
    and an enclosing member operable to enclose the embryo after the embryo is scooped up.

2. The apparatus according to claim 1 including a manually operable member for actuating said rotational movement and said longitudinal movement to move to the wall portion to scoop up the embryo.

3. The apparatus according to claim 2 wherein said manually operable member comprises a handle connected to said elongate carrying member for applying longitudinal movement to the elongate carrying member and a rotatable portion of the handle for rotating the elongate carrying member.

4. The apparatus according to claim 3 wherein the rotatable portion forms an end portion of a cylindrical handle opposite to the elongate carrying member.

5. The apparatus according to claim 1 wherein the elongate carrying member comprises a wire.

6. The apparatus according to claim 1 wherein the enclosing member comprises a cover portion carried on the remote end of the endoscope where the scoop member is pulled into cooperation with the cover portion by retraction movement of the elongate carrying member.

7. The apparatus according to claim 1 wherein the scoop member comprises a bowl with a generally semi-spherical bottom portion forming a top edge of the bowl where the top edge of the bowl extends from a lower portion of the top edge of the bowl at an end of the bowl adjacent a remote end of the elongate carrying member to a raised end wall portion of the bowl at an end of the bowl remote from the elongate carrying member and wherein the cover portion comprises a generally arched wall with side edges which cover the top edge of the bowl and an end edge of the cover portion which butts up to the raised end wall portion of the bowl.

8. The apparatus according to claim 1 wherein the scoop member and the remote end of the endoscope include cooperating locating members to allow engagement of the scoop member with the remote end only in a predetermined angular position of the scoop member around the axis of the elongate carrying member at which the enclosing member cooperates with the scoop member to enclose the scoop member.

9. An apparatus for transferring an embryo from a uterus of a female donor mammalian animal in pregnancy to a uterus of a female recipient mammalian animal and raising the embryo to full term in the recipient animal, the apparatus comprising:

an endoscope having a camera;

the endoscope having a remote end of the endoscope arranged to be inserted vaginally into the uterus of the donor animal to a location adjacent the embryo on a wall portion of the uterus of the donor animal;

the remote end of the endoscope being operable by a manually operable member to move the remote end to different positions within the uterus;

an elongate carrying member extending outwardly from the remote end of the endoscope;

a scoop member carried on the elongate carrying member to scoop up the embryo from the wall portion of the uterus;

and an enclosing member operable by relative movement of the enclosing member and the scoop member in a direction longitudinally of the elongate carrying member to enclose the scoop member after the embryo is scooped up.

10. The apparatus according to claim 9 wherein the enclosing member comprises a cover portion carried on the remote end of the endoscope where the scoop member is pulled into cooperation with the cover portion by retraction movement of the elongate carrying member.

11. The apparatus according to claim 9 wherein said manually operable member comprises a handle connected to said elongate carrying member for applying longitudinal movement to the elongate carrying member and a rotatable portion of the handle for rotating the elongate carrying member.

12. The apparatus according to claim 11 wherein the rotatable portion forms an end portion of a cylindrical handle opposite to the elongate carrying member.

13. The apparatus according to claim 9 wherein the scoop member comprises a bowl with a generally semi-spherical bottom portion forming a top edge of the bowl, where the top edge of the bowl extends from a lower portion of the top edge of the bowl at an end of the bowl adjacent a remote end of the elongate carrying member to a raised end wall portion of the bowl at an end of the bowl remote from the elongate carrying member and wherein the cover portion comprises a generally arched wall with side edges which cover the top edge of the bowl and an end edge of the cover portion which butts up to the raised end wall portion of the bowl.

14. The apparatus according to claim 9 wherein the scoop member and the remote end of the endoscope include cooperating locating members to allow engagement of the scoop member with the remote end only in a predetermined angular position of the scoop member around a longitudinal axis of the elongate carrying member at which the enclosing member cooperates with the scoop member to enclose the scoop member.

15. The apparatus according to claim 9 wherein the enclosing member includes openings allowing viewing through the openings by the camera of the endoscope.

16. The apparatus according to claim 9 further comprising
an insertion tool arranged to be carried on said elongate carrying member of said endoscope to deposit the embryo onto a wall of the uterus of the recipient animal;

and a transfer device to transfer the embryo from the scoop member to the insertion tool.

17. The apparatus according to claim 16 wherein each of the scoop member and the insertion tool is carried on respective first and second elongate carrying members for insertion into the endoscope.

18. The apparatus according to claim 17 wherein the first elongate carrying member is a wire and the second elongate carrying member is a tube for passage of fluid.

19. The apparatus according to claim 18 wherein the wire is mounted on a handle for rotation and longitudinal movement and wherein the tube is mounted on a syringe.

20. The apparatus according to claim 16 wherein a cover portion cooperates firstly with the scoop member and secondly with the insertion tool to enclose the scoop member and the insertion tool to contain the embryo.

21. The apparatus according to claim 16 wherein the insertion tool comprises a bowl into which the embryo is deposited, the bowl having fluid discharge holes for injecting discharge fluid into the bowl to expel the embryo.

22. The apparatus according to claim 16 wherein the transfer device comprises a funnel with a transverse mounting channel for the insertion tool so that fluid poured into the funnel runs into the insertion tool while contained in the channel to deposit the embryo with excess fluid spilling over.

* * * * *